(12) United States Patent
Osaka et al.

(10) Patent No.: US 7,099,802 B2
(45) Date of Patent: Aug. 29, 2006

(54) METHOD OF AND SYSTEM FOR COLLECTING INFORMATION ABOUT ANALYZING APPARATUSES, AND THE ANALYZING APPARATUS

(75) Inventors: Naoki Osaka, Kyoto-fu (JP); Tsuyoshi Morikawa, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/401,724

(22) Filed: Mar. 21, 2003

(65) Prior Publication Data

US 2003/0229475 A1 Dec. 11, 2003

(30) Foreign Application Priority Data

Jun. 5, 2002 (JP) ............................ 2002-163985

(51) Int. Cl.
G06F 11/00 (2006.01)
G06F 11/30 (2006.01)

(52) U.S. Cl. ..................... 702/188; 702/182; 340/3.1

(58) Field of Classification Search ............ 702/22–25, 702/27–32, 121, 182–185, 187, 188; 700/9, 700/19, 20, 266, 2; 340/3.1, 3.3, 3.31, 3.32, 340/3.43, 3.6, 3.61, 3.63, 3.7, 3.5, 3.51, 3.52, 340/505, 506

See application file for complete search history.

(56) References Cited

U.S. PATENT DOCUMENTS

| | | | | |
|---|---|---|---|---|
| 4,812,820 | A * | 3/1989 | Chatwin | 340/518 |
| 5,695,718 | A * | 12/1997 | Imai et al. | 422/62 |
| 5,754,426 | A * | 5/1998 | Dumais | 700/83 |
| 5,970,425 | A * | 10/1999 | Ono et al. | 702/31 |
| 6,198,482 | B1 * | 3/2001 | Okada | 345/841 |
| 6,263,347 | B1 * | 7/2001 | Kobayashi et al. | 707/201 |
| 2002/0184326 | A1 * | 12/2002 | Thomson | 709/208 |
| 2004/0098148 | A1 * | 5/2004 | Retlich et al. | 700/83 |

FOREIGN PATENT DOCUMENTS

| | | |
|---|---|---|
| JP | 04-313933 | 11/1992 |
| JP | 06-112989 | 4/1994 |
| JP | 10-282107 | 10/1998 |
| JP | 11-051942 | 2/1999 |
| JP | 11-142410 | 5/1999 |
| JP | 11-142411 | 5/1999 |
| JP | 11149431 A * | 6/1999 |

* cited by examiner

*Primary Examiner*—Marc S. Hoff
*Assistant Examiner*—Manuel L Barbee
(74) *Attorney, Agent, or Firm*—Westerman, Hattori, Daniels & Adrian, LLP.

(57) ABSTRACT

The present invention proposes an analyzing apparatus by which the operator can easily obtain the management information and/or the analysis progress information of plural apparatuses without going around to check the plural analyzing apparatuses one after another. In a liquid chromatograph 201 as an embodiment of the present invention, an individual management information collector 20 collects individual management information of the apparatus through an internal communication interface 28. Examples of the individual management information include: state of operation; operator name; control information of a liquid supply pump 4, an automatic sampler 6, a column oven 8 and a detector. A total management information collector 24 searches the network for other liquid chromatographs 202, 203, collects the individual management information of said other liquid chromatographs 202, 203, and combines the collected information and the individual management information of the liquid chromatograph 201 to form total management information. The total management information is shown to the operator on a display 25 or a web server 26 publishes the information to network 14 through a network interface 22.

4 Claims, 9 Drawing Sheets

Fig. 4

| # | Apparatus Name | Status | Column/Eluant | Operator | System Check | Memo |
|---|---|---|---|---|---|---|
| 1 | Apparatus 1 | Run 27/36 | ID000000 VP-ODS(4.6x250) | A.B. Oct. 17, 2002-Oct. 19, 2002 | Oct. 15, 2002 OK | - |
| 2 | Apparatus 2 | Start Up 1800.00 | ID000001 STR-ODS(4.6x150) | B.C. Oct. 17, 2002-Oct. 19, 2002 | Oct. 15, 2002 OK | - |
| 3 | Apparatus 3 | Power Off | - | - | Oct. 15, 2002 NG | Maintenance: Oct 22, 2001 |
| 4 | Apparatus 4 | Ready | ID000002 PC-ODS(4.6x75) | C.D. Oct. 17, 2002-Oct. 19, 2002 | Oct. 15, 2002 OK | - |

- Monitor
PUMP | SIL | OVEN | DET 0

Fig. 9

SORTED BY APPARATUS

| No. | Apparatus | Operator | Status | Scheduled Finish Time |
|---|---|---|---|---|
| 1 | Apparatus #1 | B. B. | Run | 15:08 |
| 2 | Apparatus #2 | B. B. | Run | 12:30 |
| 3 | Apparatus #3 | C. C. | Run | 09:25 |
| 4 | Apparatus #4 | A. A. | Run | 18:00 |
| 5 | Apparatus #4 | A. A. | Ready | 19:15 |

SORTED BY OPERATOR

| No. | Apparatus | Operator | Status | Scheduled Finish Time |
|---|---|---|---|---|
| 4 | Apparatus #4 | A. A. | Run | 18:00 |
| 5 | Apparatus #4 | A. A. | Ready | 19:15 |
| 1 | Apparatus #1 | B. B. | Run | 15:08 |
| 2 | Apparatus #2 | B. B. | Run | 12:30 |
| 3 | Apparatus #3 | C. C. | Run | 09:25 |

SORTED BY STATUS

| No. | Apparatus | Operator | Status | Scheduled Finish Time |
|---|---|---|---|---|
| 5 | Apparatus #4 | A. A. | Ready | 19:15 |
| 1 | Apparatus #1 | B. B. | Run | 15:08 |
| 2 | Apparatus #2 | B. B. | Run | 12:30 |
| 3 | Apparatus #3 | C. C. | Run | 09:25 |
| 4 | Apparatus #4 | A. A. | Run | 18:00 |

SORTED BY SCHEDULED FINISH TIME

| No. | Apparatus | Operator | Status | Scheduled Finish Time |
|---|---|---|---|---|
| 3 | Apparatus #3 | C. C. | Run | 09:25 |
| 2 | Apparatus #2 | B. B. | Run | 12:30 |
| 1 | Apparatus #1 | B. B. | Run | 15:08 |
| 4 | Apparatus #4 | A. A. | Run | 18:00 |
| 5 | Apparatus #4 | A. A. | Ready | 19:15 |

METHOD OF AND SYSTEM FOR COLLECTING INFORMATION ABOUT ANALYZING APPARATUSES, AND THE ANALYZING APPARATUS

The present invention relates to various analyzing apparatuses, such as liquid chromatographs or mass analyzers, and a method of and a system for collecting information about analyzing apparatuses.

BACKGROUND OF THE INVENTION

An analyzing apparatus such as a liquid chromatograph is operated with various kinds of management information. Examples of such management information include: the apparatus ID number, status information (e.g. "Run", "Finished", "Ready"); period of use of the light source or its degree of degradation (if the apparatus includes an optical detector); and the results of an operation check. Usually, an analyzing apparatus is provided with a controller for collecting such information within the apparatus and for showing the information on a display or the like to the operator. The information thus shown helps the operator to determine, for example, whether the apparatus is capable of conducting a new analysis or whether maintenance work is necessary.

Usually, a company, research institute or the like has plural analyzing apparatuses. In such case, when it is necessary to get information about each apparatus, the operator needs to go to the site of every apparatus, and check the information of every apparatus.

Many analyzing apparatuses are nowadays provided with computers. Usually, a normal personal computer is connected to an analyzing apparatus, and a dedicated program for the analyzing apparatus is installed in the computer. According to the program, the analyzing apparatus sends the results of an analysis, and the computer processes the analysis data and shows the processed data on the display. The management information of the analyzing apparatus is also sent to the computer, which is also shown on the display of the computer. If the operator wants to know the status of every analyzing apparatus, he or she must go to the computer or the analyzing apparatus to see the information on the display.

Thus, in the analysis with plural analyzing apparatuses, when the operator wants to know the state of the operation of each apparatus or to find an apparatus available for a new analysis, it is necessary to go to the site of every analyzing apparatus and check the state of the operation by the information provided by the apparatus or the computer connected to it. When many analyzing apparatuses are distributed far from one another, it is a very troublesome and time-consuming task to check the states of the operation of all the apparatuses one after another.

The problems described above concerning the management information apply also to the case where the operator must check the analysis progress information.

The analysis progress information is first explained. When, for example, plural test specimens are analyzed with a liquid chromatograph, an automatic sampler is used. Several analysis schedules are prepared beforehand where each analysis schedule determines the vial numbers of the automatic sampler and the injecting amount of the specimen of each vial. One of the analysis schedules is selected, and a sequence of plural analyses is performed using the liquid chromatograph. That is, test specimens are sampled from vials one after another with the automatic sampler as specified by the analysis schedule, analyzed by the liquid chromatograph, and the analysis data is collected. Usually, the apparatus has a display for showing the operator the progress of the sequence of analyses along the schedule. An analysis information also refers to a process of a simple analysis.

The recent trend in this case is also to use a personal computer coupled with the analyzing apparatus. Besides controlling the apparatus and processing the analysis data, the personal computer shows the operator the analysis progress information of a sequence of analyses, or the analysis progress information of a single analysis.

For improving the efficiency of analysis, companies and research institutes often use plural analyzing apparatuses and usually keep them in round the clock operation. Under such circumstances, the operator needs to perform various tasks as follows: to check the state of operation of each apparatus; to find an apparatus available for a new analysis; or to check the progress of plural analyses which the operator is in charge of. Conventionally, the operator needs to go to the site of every analyzing apparatus, and to check the state of the operation or the progress of the analysis by viewing the information provided by the apparatus or the computer connected to it. When many analyzing apparatuses are distributed far from one another, it is a very troublesome and time-consuming task to check the states of operation of all the apparatuses one after another.

To address the above problems, the present invention proposes an analyzing apparatus by which the operator can easily get the management information and/or the analysis progress information of plural apparatuses without physically going to each individual one. The present invention also proposes a method of and a system for collecting information about plural analyzing apparatuses.

SUMMARY OF THE INVENTION

Thus, the present invention proposes a first analyzing apparatus, which includes:

an individual management information collector for collecting management information of a part or parts of the analyzing apparatus as individual management information;

a network interface for connecting the analyzing apparatus to a network to transfer information to and from the network;

a total management information collector for searching the network for other analyzing apparatuses, for collecting the individual management information of said other analyzing apparatuses, for forming total management information combining the collected information and the individual management information of the analyzing apparatus, and for holding the total management information; and a display for displaying the total management information held by the total management information collector.

The present invention also proposes a method of collecting information about plural analyzing apparatuses constructed as described above. The method includes the steps of:

connecting plural analyzing apparatuses to a network;

collecting management information of the plural analyzing apparatuses connected to the network by any one of the plural analyzing apparatuses or by an information processing apparatus connected to any one of the analyzing apparatuses; and displaying the collected management information by said one of the plural analyzing apparatuses or by said information processing apparatus connected to any one of the analyzing apparatuses.

The management information includes, for example: apparatus ID number or apparatus name, status information (e.g. "Run", "Finished", "Ready"), degree of degradation of parts such as the lamp of a light source used in a detector, result of an operation check, etc.

By using the first analyzing apparatus, the operator can get information about plural analyzing apparatus while remaining at one of the plural analyzing apparatuses. Therefore, the operator can easily check whether one or some of the analyzing apparatuses needs maintenance work, or find an analyzing apparatus available for a new analysis to improve the efficiency of the operation.

The first analyzing apparatus provides such good operability that the operator need not physically go to each individual analyzing apparatus, but can stay at one (any desired one) of them to collect management information of all the analyzing apparatuses. The system of the present invention is in contrast to the conventional system where plural analyzing apparatuses (without the functionality of the present invention) are connected to a network with a server. With such a system, the operator needs to take the trouble of going to the server to get management information of the plural analyzing apparatuses. The present invention obviates such unnecessary work in laboratories or companies by using plural analyzing apparatuses.

In a preferable mode, the first analyzing apparatus further includes a network server for sending to a network client the total management information held by the total management information collector through the network interface and the network. This construction allows the operator to use a personal computer or the like connected to the network as well as the analyzing apparatuses to get the total management information.

Further, the present invention proposes a second analyzing apparatus, which includes:

an individual progress information collector for collecting analysis progress information indicative of the progress of an analysis performed by the analyzing apparatus as individual progress information;

a network interface for connecting the analyzing apparatus to a network to transfer information to and from the network;

a total progress information collector for searching the network for the other analyzing apparatuses, for collecting the individual progress information of said other analyzing apparatuses, for forming total progress information combining the collected information and the individual progress information of the analyzing apparatus, and for holding the total progress information; and a display for displaying the total progress information held by the total progress information collector.

By the second analyzing apparatus, the individual progress information collector collects the individual progress information indicative of the progress of analysis performed by the analyzing apparatus, and the total progress information collector collects the individual progress information indicative of the progress of analyses performed by other analyzing apparatuses connected to the network. The individual progress information includes, for example: status information ("Ready", "Run", "Finished", "Error") of the analysis automatically performed by each analyzing apparatus along with the steps specified by an analysis schedule; the ID or name of the operator in charge of the analysis; scheduled finish time of the analysis. In each analyzing apparatus, the total progress information collector collects the individual progress information of the other analyzing apparatuses, and combines the collected information and the individual progress information of the analyzing apparatus to form the total progress information of a preset format, typically in a list or table. The display shows the list or table containing the progress information of the analyses.

By using the second analyzing apparatus, the operator can check the progress of the analyses performed by the plural analyzing apparatuses while staying at one (any desired one) of the analyzing apparatuses. It is now easy to improve the efficiency of the analysis by finding any analyzing apparatus available at the moment or scheduled to be available soon, and starting a new analysis with that apparatus so that all the apparatuses operate efficiently all the time. Further, there is no need for the operator to physically go around to check the state of the operation of the plural analyzing apparatuses even when they are placed distant from each other. Thus, the working efficiency is improved.

Further, the present invention proposes an analyzing system having a network to which plural analyzing apparatuses and at least one client terminal are connected, wherein each of the plural analyzing apparatuses includes:

an individual progress information collector for collecting analysis progress information indicative of the progress of an analysis performed by the analyzing apparatus; and a network interface for connecting the analyzing apparatus to the network to transfer information to and from the network, and at least one of the analyzing apparatuses includes:

a total progress information collector for searching the network for other analyzing apparatuses, for collecting the individual progress information of said other analyzing apparatuses, for forming total progress information combining the collected information and the individual progress information of the analyzing apparatus, and for holding the total progress information; and a total progress information server for processing the total progress information into a preset format of data and for sending the data through the network interface and the network to the client terminal from which a request for the data has been received.

By the above analyzing system, one of the analyzing apparatuses collects the individual progress information of the other analyzing apparatuses and processes the collected information into data of a preset format, for example in a list or table. The data is then sent through the network to a client terminal, which displays the data in the preset format. The client terminal hereby may be a personal computer provided with a function of processing the analysis data obtained by the analyzing apparatus and/or a function of database server for storing and managing the data. By this analyzing system, the operator can check the progress of analyses of all the analyzing apparatuses through the client terminal.

In the case where the total progress information is processed into a list or table of data, it is preferable to provide the total progress information collector with a function of changing the displaying order of the data by selecting and/or sorting the data according to a request from the operator. By such a system, the operator can change the selection and/or order of the data according to necessity. For example, the operator can selectively check the data of only such an analysis that is being performed by plural analyzing apparatuses, or the data of only such analyses that the operator has entered into the analysis schedule by himself or herself. Such a function facilitates the visual check of the analysis progress information and hence contributes to the improvement of the working efficiency.

BRIEF DESCRIPTION OF THE DRAWINGS

FIG. 4 shows an example of the list showing the total management information created in the above embodiment.

FIG. 9 shows examples of a progress information list displayed on the screen of the personal computer.

DETAILED DESCRIPTION OF PREFERRED EMBODIMENTS

Figure 1:
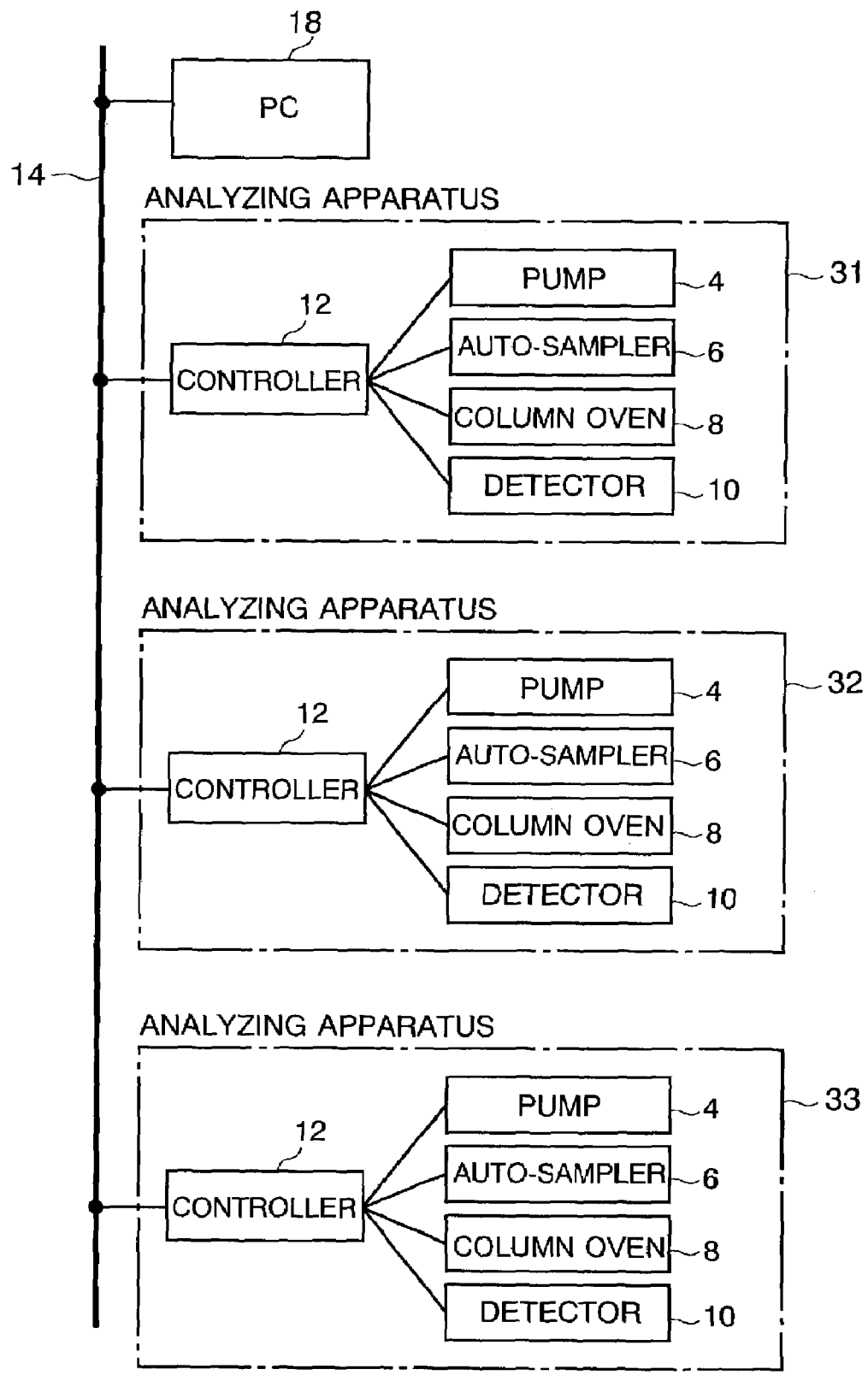
FIG. 1 is a block diagram schematically showing an embodiment of the present invention, where liquid chromatographs as the first analyzing apparatuses are connected to a network.

FIG. 1 schematically shows an embodiment of the present invention, where liquid chromatographs 31–33, each constructed as the first analyzing apparatus as described above, are connected to a network 14. The chromatographs 31–33 are identically constructed, each of which has an analysis unit having a liquid supply pump 4 for supplying an eluant to a column for separating a sample into components, a column oven 8 containing the column, an automatic sampler for injecting the sample into a passage of the eluant supplied to the column by the liquid supply pump 4, and a detector 10 for detecting components of the sample flowing out of the column. Each of the liquid chromatographs 31–33 has a controller 12 for controlling the analyzing operation of the liquid chromatograph and for collecting information about detection results obtained by the detector 10. Further, the controller 12 functions as the network interface, the individual management information collector and the total management information collector of the present invention.

In addition to the liquid chromatographs 31–33, more liquid chromatographs and/or other types of apparatuses constructed as the first analyzing apparatuses of the present invention may be connected to the network 14. Further, in this embodiment, a personal computer 18 is connected to the network 14. The personal computer 18 has a web browser, such as Internet Explorer™ produced by Microsoft Corporation, with which the operator can retrieve management information of the liquid chromatographs 31–33 or other apparatuses, if any.

Figure 2:
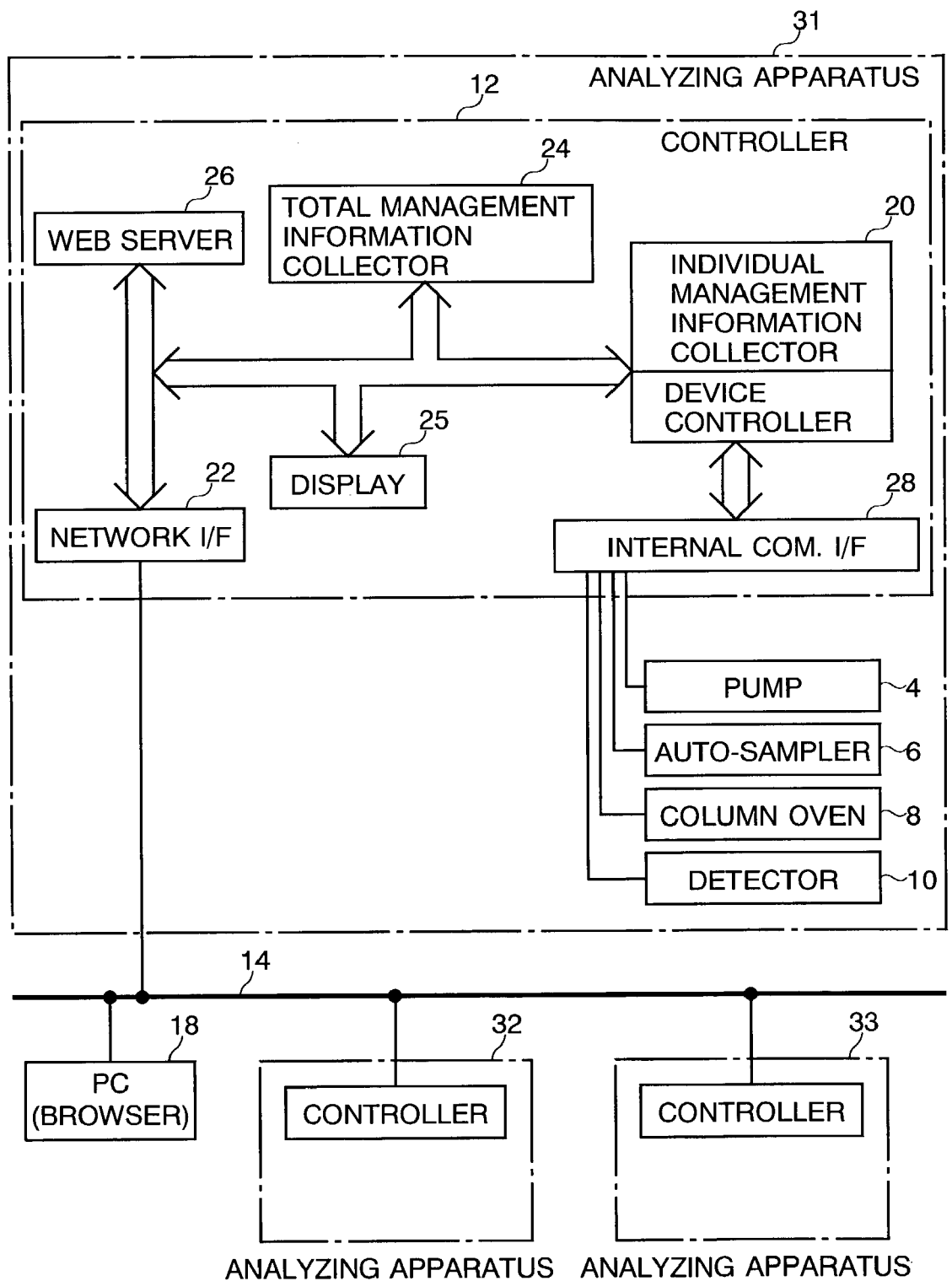
FIG. 2 is a block diagram showing the details of the functions of the controller of each liquid chromatograph shown in FIG. 1.

FIG. 2 shows the details of the functions of the controller 12 of the liquid chromatograph 31. It should be noted that the controllers of the other liquid chromatographs 32, 33 are constructed identical to the controller 12. The controller 12 is constructed using a central processing unit (CPU).

Numeral 20 denotes an individual management information collector 20, which collects various kinds of information through an internal communication interface 28 as individual management information. This information includes the following items: state of operation of the liquid chromatograph 31; identification information of the operator; information about the liquid supply pump 4, the automatic sampler 6, the column oven 10 and the detector 10, etc. The individual management information collector 20 also functions as a controller of the apparatus, which not only controls the operations of the liquid supply pump 4, the automatic sampler 6, the column oven 8 and the detector 10 but also collects information about detection results and other information through the internal communication interface 28.

Numeral 22 denotes a network interface to be connected to the network 14 for transferring information through the network 14. Numeral 24 denotes a total management information collector, which searches the network 14 for the other liquid chromatographs 32, 33 and collects the individual management information of the liquid chromatographs 32, 33 through the network interface 22. The total management information collector 24 integrates the collected information and the individual management information of the liquid chromatograph 31 into total management information, and holds the total management information. Numeral 25 denotes a display, which shows the total management information held by the total management information collector 24.

Numeral 26 denotes a web server, which is a network server for sending the total management information held by the total management information collector 24 through the network interface 22 and the network 14 to the browser running on the personal computer 18. In the following description, the browser is also represented by the numeral 18.

The operation of the system of this embodiment is then described, focusing on the liquid chromatograph 31.

The individual management information collector 20 collects the management information of the liquid chromatograph 31 at all times, where the information to be collected includes: apparatus ID number, status information, degree of degradation of parts, result of operation check, etc. The management information further includes information about the liquid supply pump 4, the automatic sampler 6, the column oven 8 and the detector 10.

Figure 3:
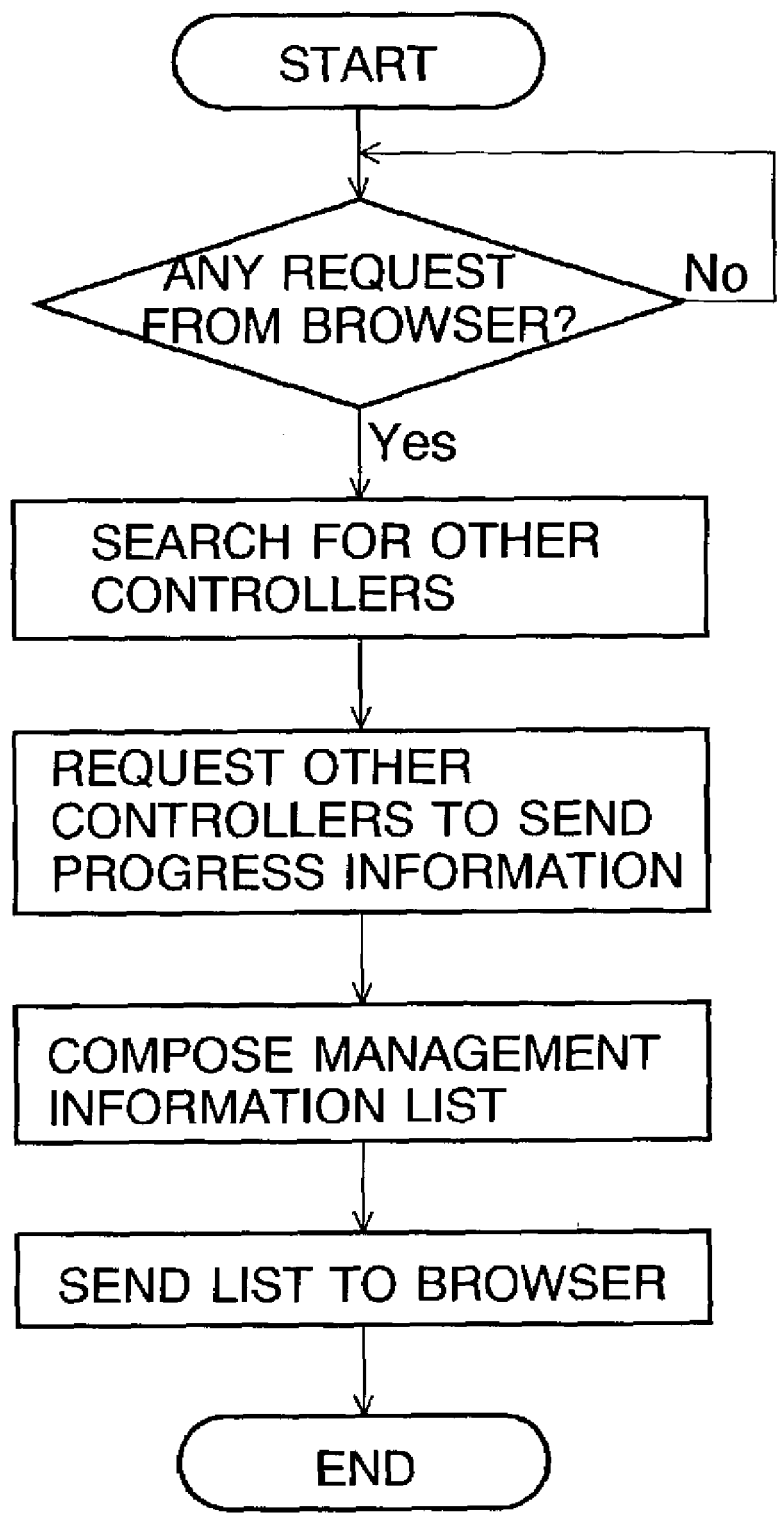
FIG. 3 is a flow chart showing an operation of the analyzing apparatus performed when a request for transfer of the total management data is received from a browser shown in FIG. 2.

On receiving a request for transfer of the total management information from the browser 18, the operation proceeds as shown in FIG. 3. First, on receipt of the request from the browser 18, the total management information collector 24 checks whether the controllers of the other liquid chromatographs 32, 33 connected to the network 14 are active. When one or more controllers are found active, the total management information collector 24 sends to each of the controllers a request for the individual management information of the liquid chromatograph 32 or 33 that includes the controller concerned. After receiving the individual management information of the other liquid chromatographs 32, 33, the total management information collector 24 combines the received (or collected) information and the individual management information of the liquid chromatograph 31 to form a list of apparatus management information as total management information. Then, the web server 26 sends the browser 18 the list of apparatus management information through the network interface 22.

It should be noted that the above description of the operation also applies to the case of the other liquid chromatographs 32, 33.

It should be also noted that, even if there is no request from the browser 18, the liquid chromatographs 31–33 collect the individual management information of the other liquid chromatographs and combines the collected information and the individual management information to form a list of total management information at all times.

FIG. 4 shows an example of the list of the total management information. The management information of four liquid chromatographs connected to the network is shown in the form of a table. For each liquid chromatograph, the table shows the following items of information: state of operation ("Run", "Power off", etc); types of column and eluant; operator name and period of use; date and result of an operation check (or system check).

Figure 5:
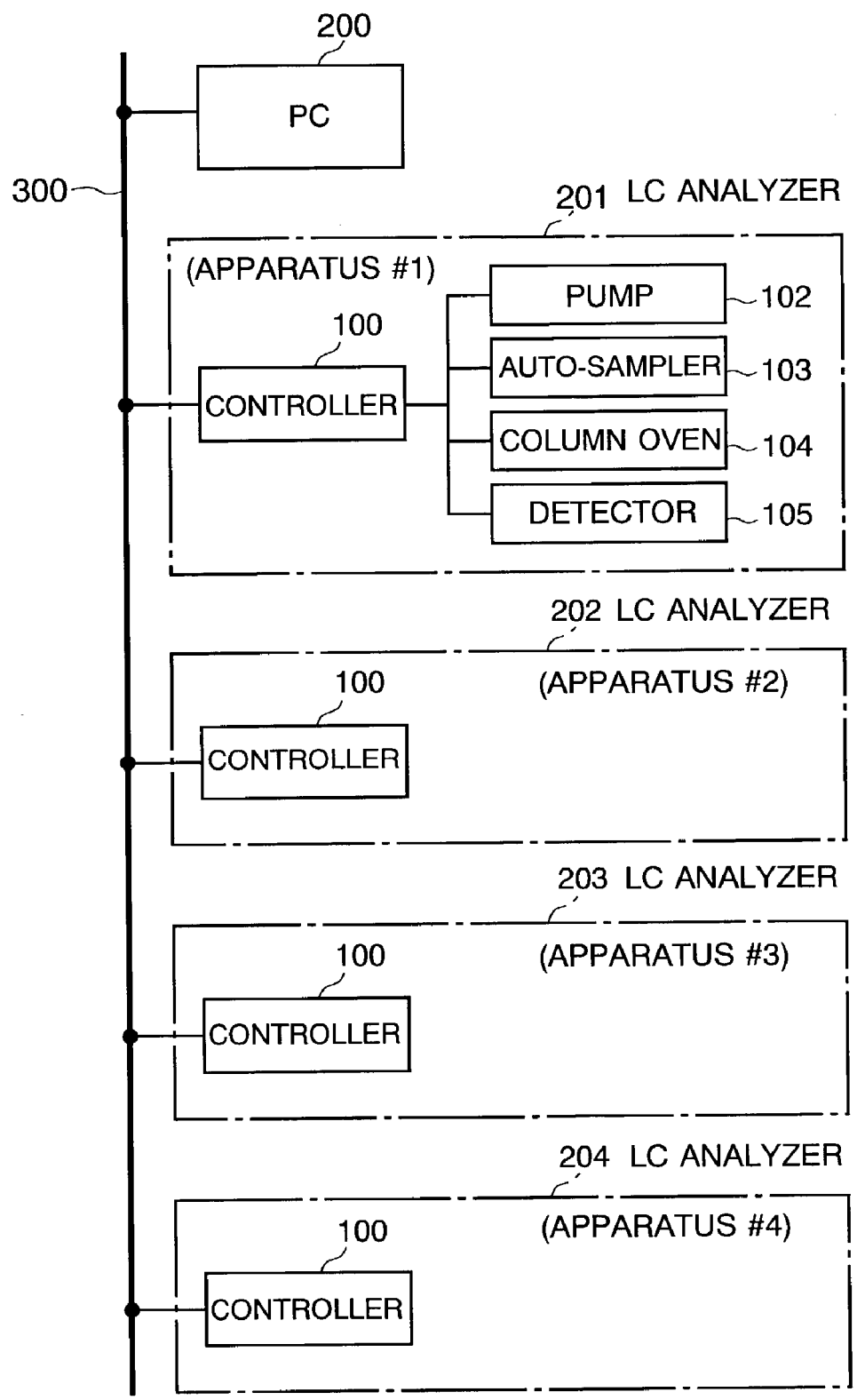
FIG. 5 is a block diagram schematically showing an analyzing system including a liquid chromatograph (LC) analyzer as an embodiment of the second analyzing apparatus of the present invention.

FIG. 5 schematically shows an analyzing system including a liquid chromatograph (LC) analyzer 201 as an embodiment of the second analyzing apparatus of the present invention. This analyzing system has a network 300 such as an intranet to which four LC analyzers 201–204 and a personal computer (PC) 200 are connected. It should be noted that the LC analyzers 202–204 have the same internal construction as the LC analyzer 201 shown in FIG. 5.

The LC analyzer 201 includes the following devices: a liquid supply pump 102 for supplying an eluant to a column for separating a sample into components; a column oven 104 containing the column; an automatic sampler 103 for injecting a liquid sample into the eluant supplied to the column by the liquid supply pump 102; and a detector 105 for detecting components of the sample flowing out of the column. Also, the LC analyzer 201 has a controller 100 for controlling the above devices according to preset analysis conditions or other parameters, and for collecting detection signals of the detector 105.

The personal computer 200 has an operational program installed. The operational program performs necessary operations on the data collected by the LC analyzers 201–204. It should be noted that a dedicated data processing apparatus for the operations on the data may be used in place of a multi-purpose personal computer.

Figure 6:
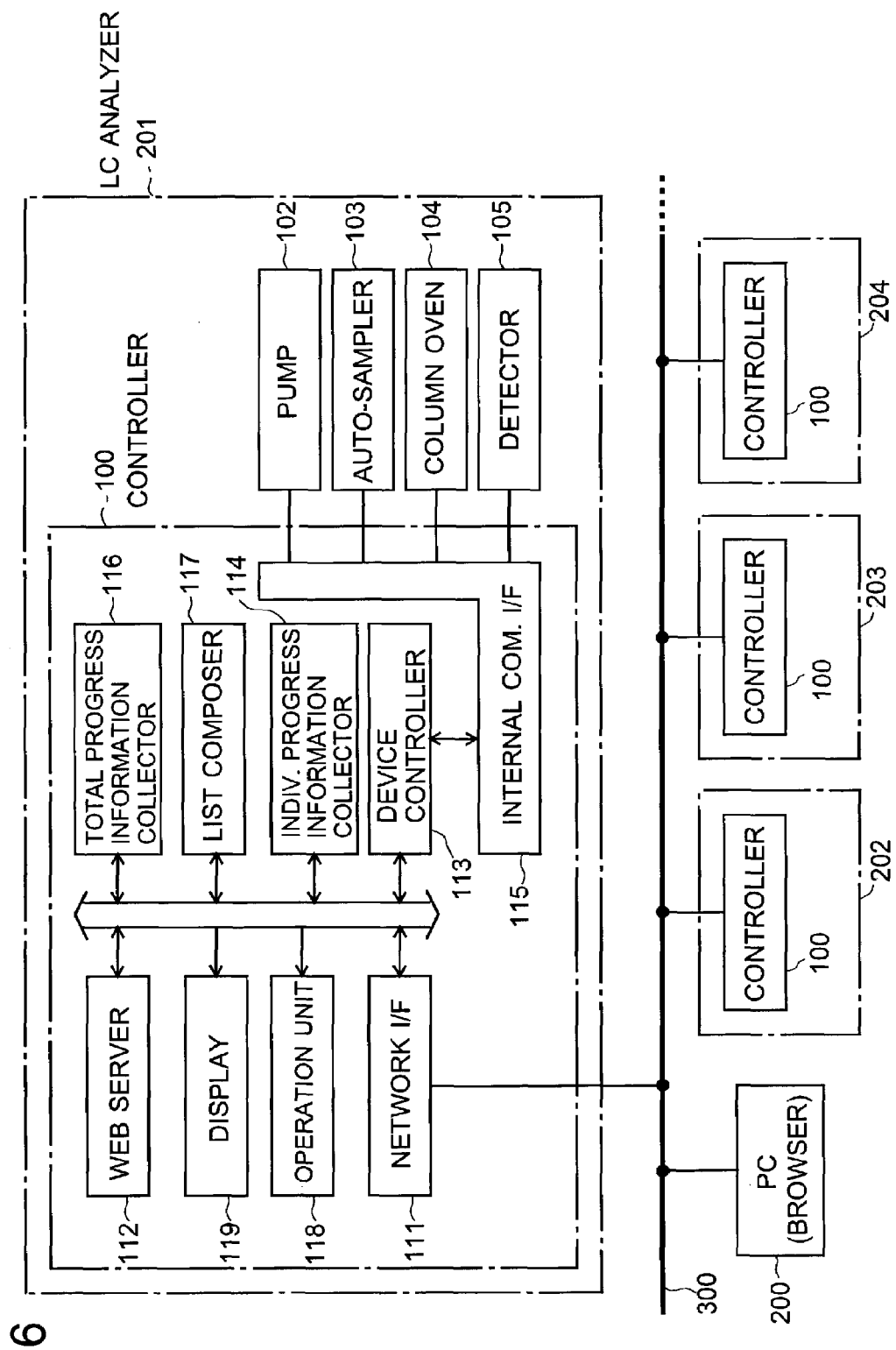
FIG. 6 is a block diagram showing the details of the functional components of the controller of the LC analyzer shown in FIG. 5.

FIG. 6 shows the details of the functional components of the controller 100 of the LC analyzer 201 shown in FIG. 5.

The controller 100 includes the following functional components: a network interface (I/F) 111 to be connected to the network 300 for transferring data through the network 300; a web server 112 for creating web contents to be published through the network 300 and sending the web contents in response to a request received through the network 300; a device controller 113 for sending control signals through an internal communication interface 115 to the liquid pump 102, the automatic sampler 103, the column oven 104 and the detector 105 included in the LC analyzer 201; an individual progress information collector 114 for collecting information about the progress of the analysis performed by the operations of the liquid supply pump 102, the automatic sampler 103, the column oven 104 and the detector 105; a total progress information collector 116 for collecting analysis progress information from the controllers 100 of the other LC analyzers 202–204 through the network 300; a list composer 117 for composing a list of analysis progress information showing the internal and external progress information collected; an operation unit 118 having operation keys to allow operators to send operation commands to the controller 100; and a display 119 for displaying characters, graphics, etc. The individual progress information collector 114 may be integrated with the device controller 113.

The personal computer 200, which is connected to the controller 100 through the network 300, has a web browser installed, e.g. Internet Explorer™ produced by Microsoft Corporation. The browser receives web contents such as programs or data from the web server 112 of the controller 100, analyzes the web contents and performs necessary operations to display characters and/or graphics in a preset format on the screen of the personal computer 200. Examples of the web contents include HTML documents, images, scripts, plug-ins, and Java™ applets.

With the above analyzing system, operators need only to operate the personal computer in a predetermined manner to control the LC analyzers 201–204 to perform a continuous, additional or extended analysis of multiple test specimens. For example, when a schedule table that specifies the conditions and order of analyses is prepared for each of the LC analyzers 201–204, the schedule table itself or a control signal indicative of the content of the schedule table is sent to the controller 100 of each of the LC analyzers 201–204. In the controller 100, the device controller 113 conducts the analysis of the test specimens, controlling the automatic sampler 103 to sample the test specimens in the order specified by the schedule table.

The controller 100 controls the liquid supply pump 102 to draw the eluant up from an eluant tank and supply the eluant to the column at a preset flow rate. The automatic sampler 103 selects the plural test specimens in a preset order, takes a sample from the selected test specimen and injects the sample into the eluant at a preset timing. The sample is introduced into the column with the eluant. In the column, which is controlled at an appropriate temperature, the sample is separated into components with the progress of time. The detector 105 detects the components flowing out of the column, and generates detection signals. The detection signals are converted into digital signals by an A/D converter, and sent to the controller 100. The controller 100 collects the data obtained by the analysis and sends the data to the personal computer 200.

Figure 7:
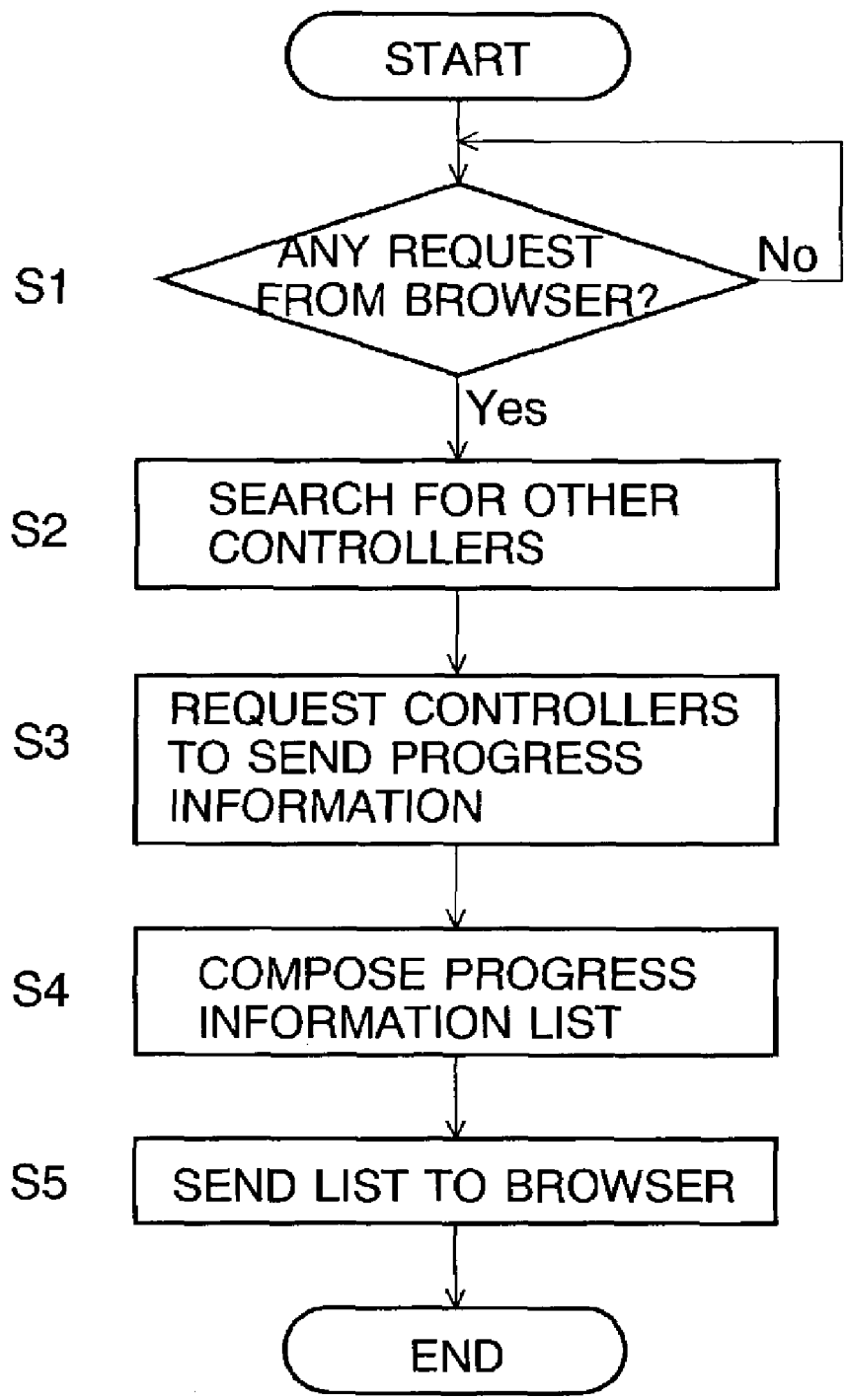
FIG. 7 is a flow chart showing an operation of the analyzing apparatus performed when an operator requests display of the total progress information.

FIG. 7 is a flow chart showing the operation of the present analyzing system performed when the operator requests a check of the progress of the analyses being performed or scheduled to be performed by the LC analyzers 201–204.

First, with the browser installed in the personal computer 200, the operator commands the system to display the analysis progress information. The command is sent from the personal computer 200 to the controller 100 of the LC analyzer 201. The controller 100 constantly monitors all the requests from the browser (Step S1). If any request has been received from the browser, the controller 100 checks whether any controller of the other LC analyzer is active on the network 300 (Step S2). Then, the total progress information collector 116 sends each of the active controllers a request for transfer of the analysis progress information collected in the LC analyzers 202–204 (Step S3). Simultaneously, the total progress information collector 116 requests the individual progress information collector 114 to collect the analysis progress information of the LC analyzer 201.

In each of the LC analyzers 201–204, the individual progress information collector 114 collects the status information of the corresponding LC analyzer as the analysis progress information at all times. For example, this information shows that the LC analyzer is performing the analysis ("Run"), the LC analyzer is ready before the start of or after the end of the analysis ("Ready"), or the analysis is halted or has been terminated due to some trouble ("Error"). Thus, the individual progress information collector 114 holds the latest status information of the corresponding LC analyzer. Therefore, by collecting the individual progress information of all the LC analyzers 201–204, the total progress information collector 116 of the LC analyzer 201 can collect and hold the latest progress information of the LC analyzers 201–204 connected to the network 300.

After that, the list composer 117 combines the analysis progress information collected by the individual progress information collector 114 of the LC analyzer 201 and the analysis progress information collected from the controllers 100 of the LC analyzer 202–204 to form a progress information list (Step S4). The web server 112 sends the data of the progress information list through the network interface 111 to the personal computer 200. In the personal computer 200, the browser processes the data and displays the progress information list on the screen.

Figure 8:
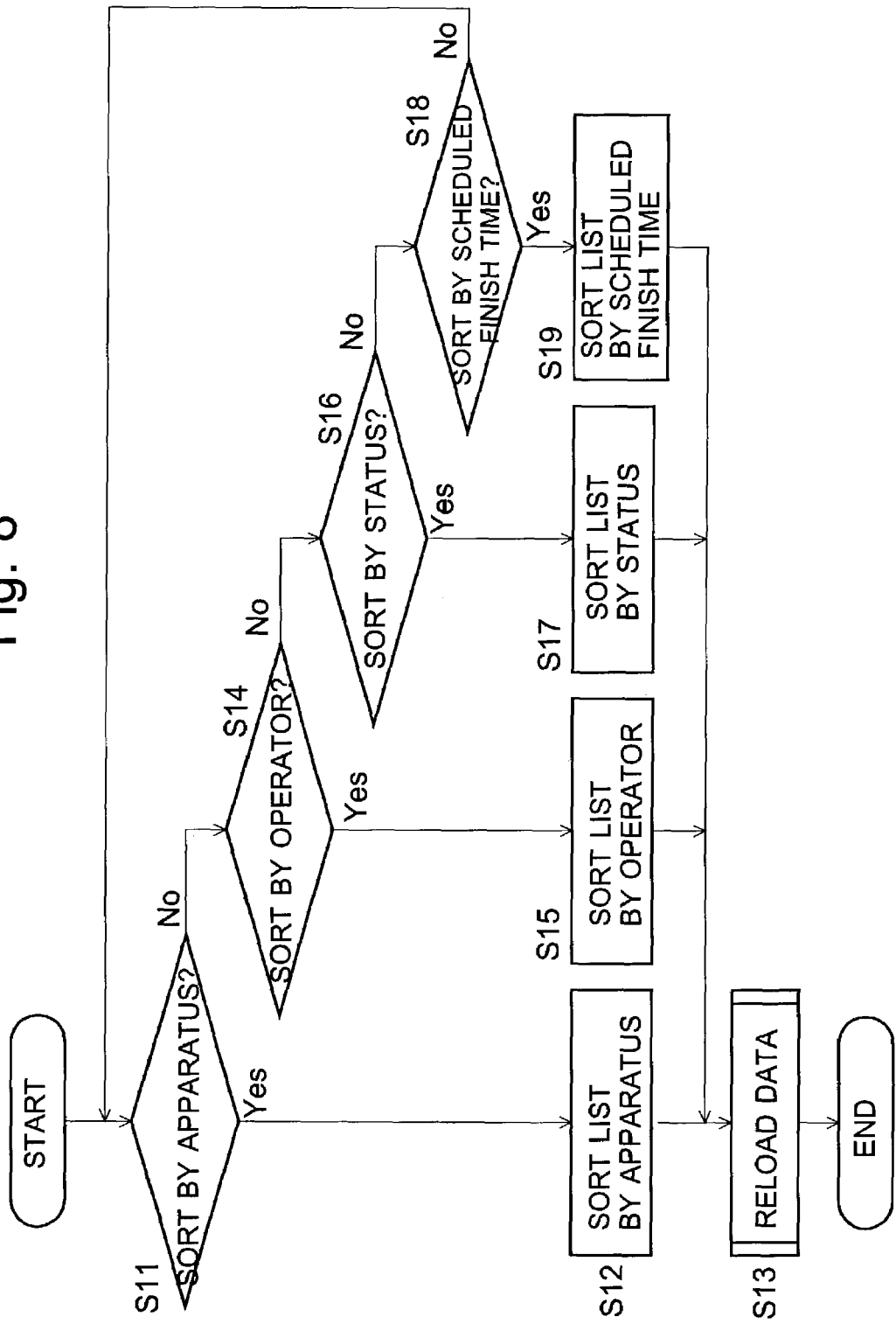
FIG. 8 is a flow chart showing a sorting process performed by a list composer.

After the progress information list is displayed on the browser window, or before that, when the operator has made a preset operation with the personal computer 200 to command the system to sort the list by a certain sort key, the command is forwarded via the web server 112 to the list composer 117, which performs the sorting of the list. FIG. 8 shows a flow chart of the sorting process performed by the list composer 117.

First, it is determined whether "Apparatus" is designated as the sort key (Step S11). If "Apparatus" is designated, the list is sorted by the apparatus name (Step S12), and the sorted list is sent to the browser for reload of data (Step S13). The first table in FIG. 9 shows an example of the list sorted by the apparatus name. If "Apparatus" is not designated, it is determined whether "Operator" (i.e. the name of the operator in charge of the analysis) is designated as the sort key (Step S14). If "Operator" is designated, the list is sorted by the operator name (Step S15), and the sorted list is sent to the browser (Step S13). The second table in FIG. 9 shows an example of the list sorted by the operator name. If "Operator" is not designated, it is determined whether "Status" is designated as the sort key (Step S16). If "Status" is designated, the list is sorted by the status information (Step S17), and the sorted list is sent to the browser (Step S13). The third table in FIG. 9 shows an example of the list sorted by the status information. If "Status" is not designated, it is determined whether "Scheduled Finish Time" is designated as the sort key (Step S18). If "Scheduled Finish Time" is designated, the list is sorted by the scheduled finish time (Step S19), and the sorted list is sent to the browser (Step S13). The fourth table in FIG. 9 shows an example of the list sorted by the scheduled finish time.

As shown in FIG. 9, the progress information of the four LC analyzers 201–204 connected to the network 300 is presented in the form of a table, where the data are sorted in an easy-to-view order designated by the operator. Therefore, the operator has only to view only one table to check the status of plural LC analyzers performing the analyses that the operator entered in the analysis schedule.

It should be noted that the sorting process may be further modified. For example, it is possible to allow the operator to designate whether to sort the list in the ascending order or in the descending order.

In the above embodiment, the personal computer 200 is used to give commands to the controller 100 of the LC analyzer 201, and to display the progress information list. It is also possible to give the commands through the operation unit 118 of the LC analyzer 201, and to display the progress information list on the screen of the display 119. Further, it is possible to use any one of the other LC analyzers 202–204 in place of the LC analyzer 201 to perform the above-described operations, because the LC analyzers 201–204 are identically constructed. It is also possible to exclusively use the LC analyzer 201 to collect the progress information of all the LC analyzers 201–204 and to construct the other LC analyzers 202–204 without the total progress information collector 116, the list composer 117 and other unnecessary functional components.

What is claimed is:

1. An analyzing apparatus, comprising:
   an individual progress information collector for collecting analysis progress information indicative of a progress of an analysis performed by the analyzing apparatus as individual progress information;
   a network interface for connecting the analyzing apparatus to a network to transfer information to and from the network;
   a total progress information collector for searching the network for other analyzing apparatuses, for collecting the individual progress information of said other analyzing apparatuses, for forming total progress information combining the collected information and the individual progress information of the analyzing apparatus, and for holding the total progress information; and
   a display for displaying the total progress information held by the total progress information collector.

2. The analyzing apparatus according to claim 1, where the total progress information collector changes a displaying order of data according to an externally given instruction.

3. An analyzing system including a network to which a plurality of analyzing apparatuses and at least one client terminal are connected, wherein each of the plurality of analyzing apparatuses comprises:
   an individual progress information collector for collecting analysis progress information indicative of a progress of an analysis performed by the analyzing apparatus; and
   a network interface for connecting the analyzing apparatus to the network to transfer information to and from the network, and
   at least one of the plurality of the analyzing apparatuses comprises:
   a total progress information collector for searching the network for other analyzing apparatuses, for collecting the individual progress information of said other analyzing apparatuses, for forming total progress information combining the collected information and the individual progress information of the analyzing apparatus, and for holding the total progress information; and
   a total progress information server for processing the total progress information into a preset format of data and for sending the data through the network interface and the network to the client terminal from which a request for the data has been received.

4. The analyzing system according to claim 3, where the total progress information collector changes a displaying order of data according to an externally given instruction.

* * * * *

UNITED STATES PATENT AND TRADEMARK OFFICE
CERTIFICATE OF CORRECTION

PATENT NO. : 7,099,802 B2
APPLICATION NO. : 10/401724
DATED : August 29, 2006
INVENTOR(S) : Naoki Osaka et al.

It is certified that error appears in the above-identified patent and that said Letters Patent is hereby corrected as shown below:

On the Title Page, Item (22); Filing Date

Please correct the Filing Date which should read, --Mar. 31, 2003--.

Signed and Sealed this

Sixth Day of March, 2007

JON W. DUDAS
*Director of the United States Patent and Trademark Office*